United States Patent [19]

Goodson et al.

[11] 4,256,985

[45] Mar. 17, 1981

[54] SPECIFICITY OF SEMICONDUCTOR GAS SENSOR

[75] Inventors: Louis H. Goodson, Kansas City, Mo.; William B. Jacobs, Overland Park, Kans.

[73] Assignee: Midwest Research Institute, Kansas City, Mo.

[21] Appl. No.: 913,280

[22] Filed: Jun. 7, 1978

[51] Int. Cl.³ ............................................. G01N 27/12
[52] U.S. Cl. ....................................... 307/308; 73/23; 250/301; 328/1; 340/631; 340/634
[58] Field of Search ............................ 307/308; 328/1; 250/301; 324/71 SN; 340/631, 632, 634; 73/23

[56] References Cited

U.S. PATENT DOCUMENTS

| 3,864,628 | 2/1975 | Klass et al. ........................ 73/23 X |
| 3,922,656 | 11/1975 | Horvath et al. .................. 340/632 X |
| 3,961,248 | 6/1976 | Kawamura ....................... 324/71 SN |
| 4,088,986 | 5/1978 | Boucher ............................ 340/634 X |

Primary Examiner—John Zazworsky
Attorney, Agent, or Firm—Otto M. Wildensteiner; Harold P. Deeley, Jr.; Herbert E. Farmer

[57] ABSTRACT

A gas sensor unit designed to indicate the presence of hydrocarbon vapors but be insensitive to carbon monoxide. The unit comprises two TGS sensors, one covered by a semi-permeable membrane and the other uncovered; the uncovered sensor responds to both crude oil and carbon monoxide, the covered sensor responds only to carbon monoxide. In one embodiment, the two sensors are connected in series; the total response of both sensors and the difference in response between the two sensors are measured, and changes in the parameters indicate the presence of an oil spill. In another embodiment, each sensor's output is compared with its reference voltage; if the uncovered sensor has an output that is higher than its reference while the covered one does not, the presence of an oil spill is indicated.

7 Claims, 3 Drawing Figures

SPECIFICITY OF SEMICONDUCTOR GAS SENSOR

STATEMENT OF GOVERNMENT INTEREST

The invention described herein was made in the course of a contract from the U.S. Government and may be manufactured and used by or for the Government for governmental purposes without the payment of any royalties thereon or therefor.

BACKGROUND

The present invention is an oil spill detector which is intended to monitor a limited area around it. The unit is designed to be mounted on a buoy or on a seawall and to detect the presence of fresh oil spills that are in the channel marked by the buoy or seawall. Solid state sensors are the preferred sensing devices for this type of detector because of their simplicity and reliability; they have no moving parts whose operation could be disrupted either by the corrosive atmosphere or by the motion of the sea if buoy mounted.

The sensors used in the present invention are made by Figaro Engineering Inc. of Osaka, Japan and are known as Taguchi Gas Sensors, or TGS sensors, model 812. The TGS model 812 sensor is a heated semiconductor chip which increases its conductivity when certain organic vapors are absorbed on its surface. The principal active ingredient in the semiconductor chip is stannic oxide, which is heated by a resistance heater incorporated into the chip. Heating minimizes the sensitivity of the chip to water vapor and at the same time speeds the reversal of the adsorption process so that the sensor quickly recovers after its exposure to organic vapors. The sensors require a heater voltage of 5.0+0.2 volts and a circuit voltage of 10–15 volts.

Uncovered TGS sensors have one drawback to being used as oil spill detectors: they are sensitive to airborne gaseous contaminants such as the carbon monoxide in engine exhaust as well as hydrocarbon vapors. An uncovered sensor would thus respond to a passing ship just as it would to an oil spill. Attempts to find a membrane that would pass crude oil vapors but not carbon monoxide were unsuccessful; hence the present invention was devised to overcome the problem.

Accordingly, it is an object of the present invention to provide a hydrocarbon vapor detector unit that is insensitive to carbon monoxide.

It is a further object to provide a unit of the above type which uses solid state devices as sensors.

It is a further object to provide a unit of the above type which can be mounted either on a buoy or seawall.

SUMMARY

Briefly, the present invention comprises two TGS model 812 sensors; one is uncovered, the other is covered by a membrane that is permeable to carbon monoxide but not crude oil vapors. In one embodiment the two sensors are connected in series, and the total response of both sensors and the difference in response between the two sensors are measured. The presence of an oil spill is indicated when both voltages increase.

In another embodiment the two sensors are mounted in parallel and the output of each is compared with its reference voltage. If the output from the covered sensor is below its reference voltage while the output voltage from the uncovered sensor is above its reference voltage, the presence of an oil spill is indicated.

DESCRIPTION OF THE PREFERRED EMBODIMENTS

Figure 1:
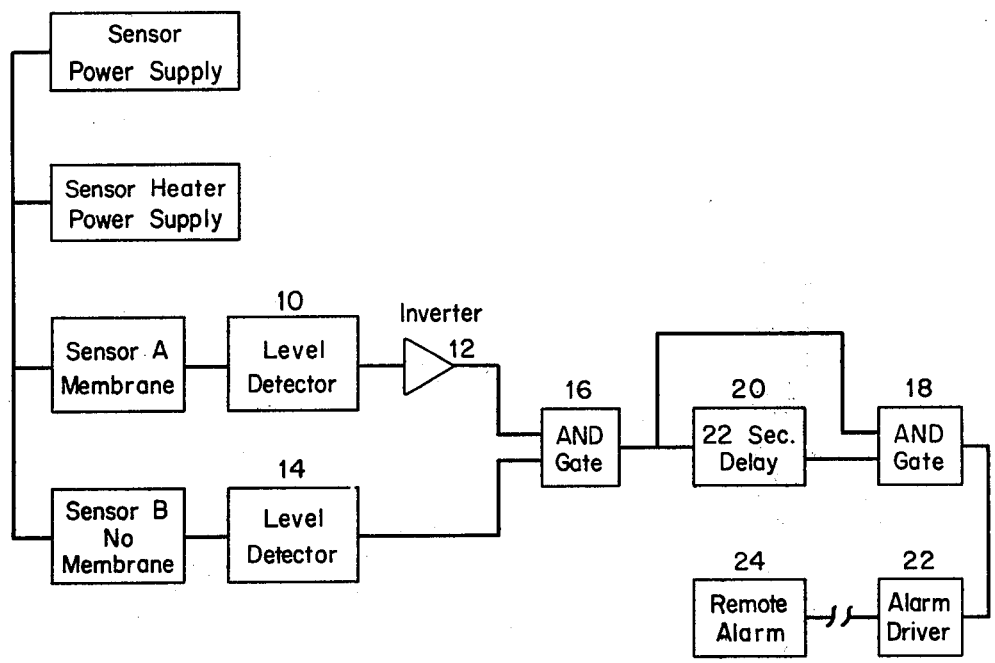
FIG. 1 shows a block diagram of the electronic circuit of one of the preferred embodiments of the present invention.

FIG. 1 shows a block diagram of the embodiment wherein the signal from each sensor is compared with its reference voltage. In this embodiment, the signal from sensor A goes into level detector 10 and then into inverter 12; if the signal from sensor A is above a certain value level detector 10 feeds a high signal into inverter 12 which is inverted into a low signal; if it is below this level a low signal is fed into inverter 12 and inverted into a high signal. The signal from sensor B is likewise determined to be either high or low by level dectector 14 but is not inverted. Both signals are fed into AND gate 16, which produces an output only when both signals are high. The signal from AND gate 16 is divided, one part going directly into AND gate 18 and the other going through a 22 second delay circuit 20 and then into AND gate 18. AND gate 18 produces an output only when it receives two high signals; this output then actuates alarm driver 22, which operates remote alarm 24.

Sensor A is covered by a membrane which is permeable to carbon monoxide (CO) but not permeable to hydrocarbon vapors. It was found that rubber dental dam material, which is a natural gum rubber sheet that is available from any dental supply house, was permeable in the above manner. Sensor A is surrounded by a wire mesh cylinder and the cylinder is covered by this rubber dental dam material so that sensor A is completely sealed within the rubber dental dam. Thus whatever reaches sensor A must first pass through the membrane.

Operation of this embodiment is as follows. In the normal unresponsive state (i.e., no output from either sensor A or B), the signals from sensors A and B are low and so are the signals from both level detectors; however, the signal from level detector 10 is inverted into a high signal; this high signal from inverter 12 and the low signal from level detector 14 do not meet the criterion for AND gate 16, hence there is no signal from it.

When a ship goes past and the detector is exposed to its exhaust fumes, which contain carbon monoxide (CO), both sensors respond since the membrane over sensor A is permeable to CO. The high output from sensor A is inverted into a low signal, however, and again there is a high signal and a low signal at AND gate 16 and once again there is no signal from it.

When hydrocarbon vapors are present, sensor B responds and there is a high signal output from it. Sensor A, sealed within the dental dam membrane, does not respond; but the output of level detector 10, which is a low signal, is inverted into a high signal by inverter 12. Thus there are two high signals at AND gate 16 and there is an output from it. This output is then divided, one part going directly into AND gate 18 and the other going into 22 second delay circuit 20. The purpose of the delay circuit is to prevent the detector from sounding an alarm for every little oil spill that is detected, since a busy ship channel will have a considerable number of small oil patches floating on it. It was arbitrarily decided that an oil slick that stayed within range of the present detector for 22 seconds was of sufficient size to warrant the sounding of an alarm. This delay can be different for different applications; a shorter delay will cause the alarm to be sounded for smaller oil spills, a longer delay will make the detector respond only to larger spills. Before the expiration of the preset delay period there is only one high signal at AND gate 18 and there is thus no output to alarm driver 22. If hydrocarbon vapors are still present at the expiration of the delay period the high signal from the delay circuit will also reach AND gate 18 and the output from this will cause alarm driver 22 to sound the alarm.

Figure 2:
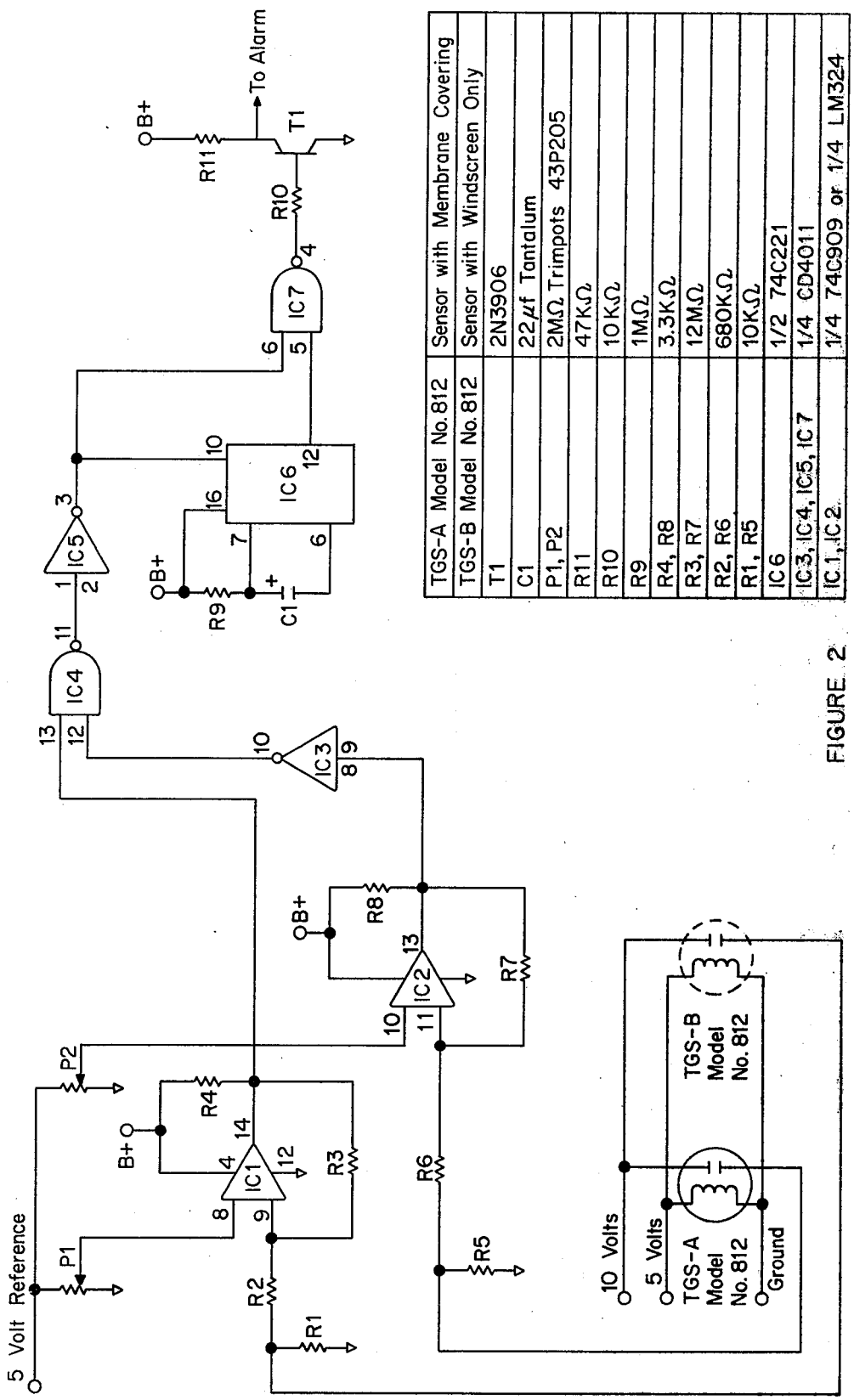
FIG. 2 is a schematic of the electronics for the embodiment shown in FIG. 1.

FIG. 2 shows the circuitry for the sensor electronics for the configuration of FIG. 1.

Figure 3:
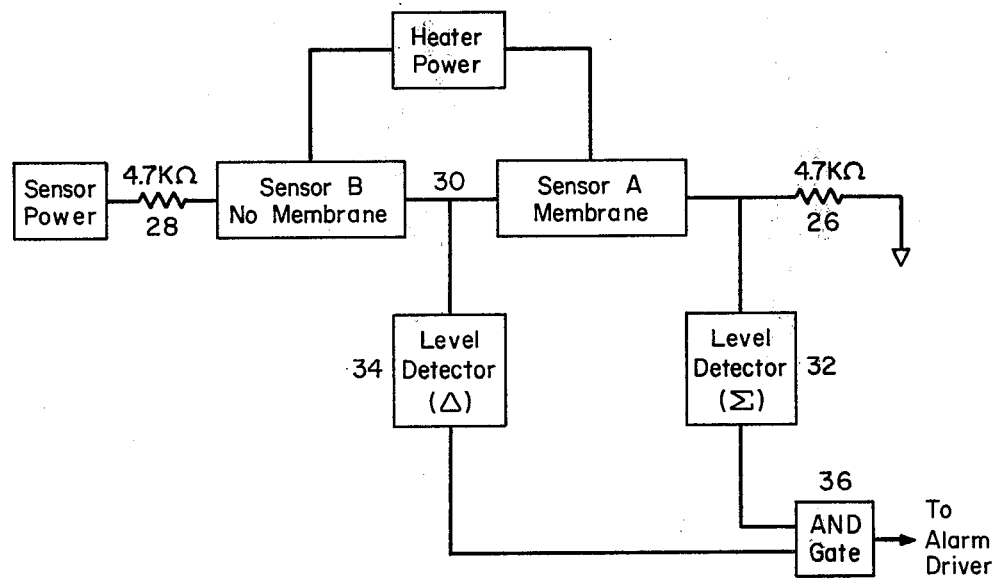
FIG. 3 shows the circuit for another of the preferred embodiments of the present invention.

FIG. 3 shows the circuitry for the second embodiment of the present invention, which measures the difference in the voltage drops across the two sensors and the total voltage drop across both sensors. Sensors A and B have their sensing elements connected in series and also in series with two resistors 26 and 28. The voltage across resistor 26 is called the summation signal, $\Sigma$, and the voltage measured at the midpoint 30 between the two sensors is called the difference signal, $\Delta$. Summation signal $\Sigma$ goes into level detector 32 and difference signal $\Delta$ goes into level detector 34; the signals from both level detectors go into AND gate 36, which operates the alarm driver and remote alarm (not shown), when both signals increase by certain amounts.

Operation of this embodiment is as follows. When there are no ships or hydrocarbon vapors in the area the summation signal $\Sigma$ is aproximately 0.5 volts and the difference signal $\Delta$ is approximately 4 volts; level detectors 32 and 34 are set to respond with a low signal at these voltages. In the presence of CO the resistance of both sensors drops equally; there is no change in the difference signal $\Delta$, but the summation signal $\Sigma$ increases. Level detector 32 responds with a high signal output and level detector 34 continues to give a low signal output; since AND gate 36 requires two high signals before it sends a signal to the alarm driver, the detector does not respond to CO.

In the presence of hydrocarbon vapors there is a decrease in the resistance of uncovered sensor B only; this causes an increase in both the difference signal $\Delta$ and the summation signal $\Sigma$. Level detectors 32 and 34 are set to respond to these increased signals by sending high signals to AND gate 36, which activates the alarm driver. No time delay is shown in FIG. 3 although one would probably be necessary in an operational unit as discussed above. In the configuration tested the alarm was triggered when the difference signal $\Delta$ rose one volt and the summation signal $\Sigma$ rose to 0.8 volts or more.

In an operational detector the sensors must be kept from getting wet (because wet sensors respond like sensors exposed to hydrocarbon vapors), they must be protected from wind gusts so that noisy baseline voltages are avoided, and they must be readily accessible to hydrocarbon vapors. Thus the detector must be in a well-ventilated shelter that has louvers on the ventilation opening which are arranged so that there are no straightline paths from outside the shelter to the sensors. There should also be screens over the louvers to keep out insects, etc.

The rubber dental dam material that covers one sensor is not totally impermeable to hydrocarbon vapors. In time hydrocarbon vapors will get through it, but for the time periods involved in the present application (i.e., 22 seconds) it can be considered impermeable to hydrocarbon vapors.

The present invention can use sensors other than TGS model 812 sensors, so long as they have the same operating characteristics. Additionally, the membrane-covered sensor can be a sensor that is optimized for CO detection, such as the TGS model 711 sensor for example.

What is claimed is:

1. An oil spill detector comprising: a pair of electronic sensors responsive to both hydrocarbon vapors and other airborne contaminants the detection of which is not desired; a semipermeable membrane covering only one of said sensors, said membrane being impermeable to said hydrocarbon vapors; and electronic circuitry means connected to said sensors for discriminating between the presence of said hydrocarbon vapors and the presence of said other airborne contaminants.

2. An oil spill detector as in claim 1 wherein said sensors are connected in series.

3. An oil spill detector as in claim 2 wherein said electronic circuitry means comprises a means to measure (1) the difference between the voltage drop across said covered sensor and the voltage drop across said uncovered sensor, and (2) the total voltage drop across both of said sensors.

4. An oil spill detector as in claim 3 wherein said electronic circuitry means further comprises a voltage level detector for each measured voltage and an AND gate connected to said voltage level detectors.

5. An oil spill detector as in claim 1 wherein said sensors are connected in parallel.

6. An oil spill detector as in claim 5 wherein said electronic circuitry means comprises (1) a voltage level detector and an inverter connected in series with the semi-permeable membrane covered one of said pair of electronic sensors, (2) a voltage level detector connected in series with the uncovered one of said pair of electronic sensors, and (3) a first AND gate connected to the circuits defined in (1) and (2) above.

7. An oil spill detector as in claim 6 wherein said electronic circuitry means further comprises a time delay circuit in series with said first AND gate, a bypass around said time delay circuit, and a second AND gate connected to said time delay circuit and said bypass.

* * * * *